United States Patent [19]

Cremer et al.

[11] Patent Number: 4,748,980

[45] Date of Patent: Jun. 7, 1988

[54] APPLICATION OF CUTS TO BIOLOGICAL MATERIAL

[76] Inventors: Christoph Cremer, 67 Panoramastrasse; Thomas Cremer, 61 Weinbrennerstrasse; Karl O. Greulich, 25-27 Ploeck; Shamci Monajembashi, 5 Rahmengasse, all of 6900 Heidelberg; Juergen Wolfrum, 2 Suedring, Rosdorf, all of Fed. Rep. of Germany

[21] Appl. No.: 81,543

[22] Filed: Aug. 4, 1987

Related U.S. Application Data

[63] Continuation of Ser. No. 800,311, Nov. 21, 1985, abandoned.

[30] Foreign Application Priority Data

Nov. 23, 1984 [DE] Fed. Rep. of Germany ....... 3442658
Mar. 15, 1985 [DE] Fed. Rep. of Germany ....... 3509273

[51] Int. Cl.$^4$ .............................................. A61N 5/06
[52] U.S. Cl. ................................. 128/303.1; 128/362
[58] Field of Search ...................... 128/303.1, 362, 395; 219/121 L, 121 LG, 121 LM, 121 LN

[56] References Cited

U.S. PATENT DOCUMENTS

| | | | |
|---|---|---|---|
| 3,297,876 | 1/1967 | De Maria | 219/121 L |
| 3,410,203 | 11/1968 | Fischbeck | 219/121 L |
| 3,710,798 | 1/1973 | Bredmeier | 128/303.1 |
| 3,769,963 | 11/1973 | Goldman et al. | 219/121 LN |
| 3,782,823 | 1/1974 | Kantorski et al. | 219/121 L |
| 4,289,378 | 9/1981 | Remy et al. | 128/303.1 |
| 4,520,816 | 6/1985 | Schachar et al. | 128/395 |
| 4,548,082 | 10/1985 | Engebretson et al. | 128/746 |
| 4,556,057 | 12/1985 | Hiruma et al. | 128/395 |

FOREIGN PATENT DOCUMENTS

| | | | |
|---|---|---|---|
| 1478919 | 5/1966 | France | 219/121 L |
| 1442002 | 7/1976 | United Kingdom | 219/121 LG |

OTHER PUBLICATIONS

"Atomic Resolution Scanning Ion Microscope", by R. McCorkle et al.; IBM Technical Disclosure Bulletin; vol. 22; #12, 5/80, p. 5476.

"Spatially Coherent Beam Formation & Mode Locking of an Array of Solid State Lasers", by E. Rutz; IBM Technical Disclosure Bulletin; vol. 20; #4; 9/77, pp. 1594–1595.

"Precise Perforations Every Time", by H. Silvers et al.; The Tool and Manufacturing Engineer; 11/69, pp. 46–49.

"A UV Nitrogen Laser use a Micro-Scalpel for All Research", by Isenberg et al., Biomedizinische Technik, vol. 21, pp. 23–24, 6/76.

Primary Examiner—Lee S. Cohen
Assistant Examiner—David Shay
Attorney, Agent, or Firm—Keil & Weinkauf

[57] ABSTRACT

In a method for the application of cuts, perforations and/or microlesions to biological material, such as cell agglomerates, individual cells or chromosomes, by means of laser pulses fed into a microscope, the laser pulses are focussed to a cross-section which is limited by diffraction phenomena, and the nth order diffraction maxima (n=1, 2, 3, . . . ) of the laser pulses are used to apply the cuts.

2 Claims, 1 Drawing Sheet

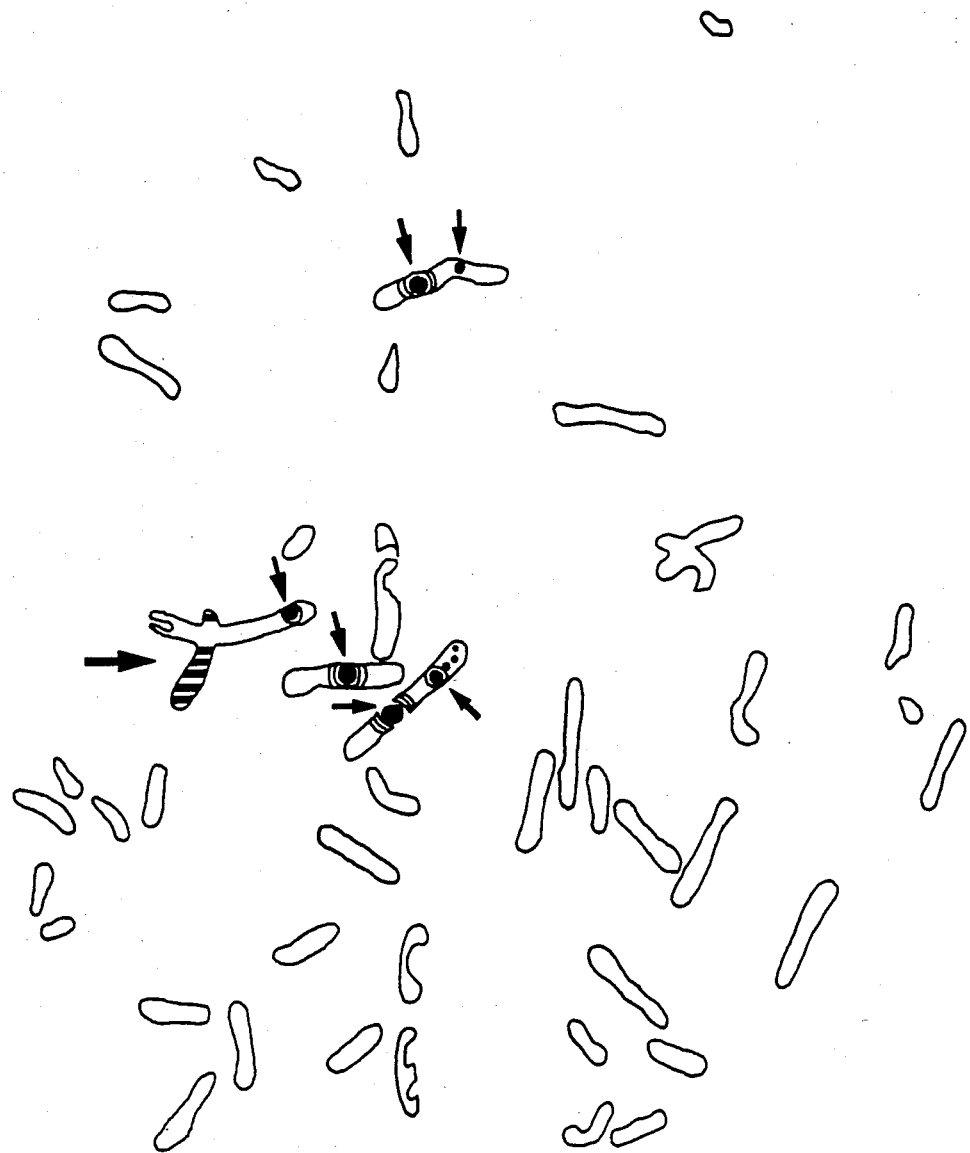

APPLICATION OF CUTS TO BIOLOGICAL MATERIAL

This application is a continuation of application Ser. No. 06/800,311, filed on Nov. 21, 1985, now abandoned.

BACKGROUND OF THE INVENTION

The present invention relates to a method for processing biological material of various forms and origins by means of laser pulses which are generated with a laser system consisting of a pumping laser and a dye laser and which are focussed in a microscope to the theoretically possible limit.

It is known that laser light, in particular that from dye lasers, has a very low beam divergence and can therefore be very well focussed. To achieve this, it is in principle sufficient to image the laser beam in a focal plane through a lens or a system of lenses. In the case of the application of lenses of long focal length, a focus is obtained which is not very well defined in terms of its depth (in the direction of propagation of the light). It is however possible, by feeding the light into a microscope, to make use of the very short focal length of the microscope objective in order to generate a focal spot which has a small depth and the cross-section of which corresponds to the wavelength of the light.

A device of the type mentioned above is known from Science 213 (1981), pages 505 to 513, wherein an Nd-YAG laser pumps a dye laser, the pulses from which are fed into a microscope. At pulse lengths of 15 ns, this system was tuneable in the range from 217 to 800 nm. On the assumption of a rectangular pulse shape with time, the indicated peak power levels of $10^5$ W give a calculated pulse energy of 1.5 mJ; because of the irregular pulse shape typical in the case of lasers of this type, the pulse energy might actually have been from 0.5 to 0.7 mJ. The known device could be operated not only with tuneable pulses 15 ns in length but at three fixed wavelengths—266, 532 and 1064 nm—also with picosecond pulses (25 ps).

This device was employed to produce point lesions in chromosomes, subcellular organelles and nerve cells. From the deficits caused thereby, conclusions were drawn as to the function of the irradiated parts.

SUMMARY OF THE INVENTION

It is an object of the present invention to apply very-fine lesions, perforations and equidistant cuts to elongate biological materials. In this connection, the general opinion was that it would be possible to achieve this object by quantitatively precisely defined reduction of the pulse energy, compared with the above-indicated pulse energies. Threshold effects could thus be used in such a manner as to produce lesions smaller than that caused by the wavelength of the light employed.

We have found that this object is achieved, surprisingly, by a step in the opposite direction by means of the features of the claims.

By the application of an excimer laser of high power and a dye laser also of high power, it was possible to increase the pulse energy by a further order of magnitude to 15 mJ per pulse. As a result of this, diffraction phenomena, which are in theory always to be expected when a laser is coupled with a microscope and which are as a rule regarded as undesirable secondary effects, became so strong that these diffraction phenomena themselves could be utilized to apply lesions.

BRIEF DESCRIPTION OF THE DRAWINGS

The figure is a view, as seen through a microscope, of elongate biological material the dark spots indicate lesions created by the focussed beam of the laser, the lines centered around the spots indicate lesions created in the material by diffraction maxima created by the laser beam passing through the diaphragm apertures of the microscope.

DESCRIPTION OF THE PREFERRED EMBODIMENTS

The method according to the invention is thus based essentially on the following conditions:
1. Application of a pumping laser of high power (eg. an excimer laser).
2. Tuneability by means of a dye laser connected downstream.
3. Feeding of the laser radiation into a microscope.
4. Utilization of diffraction phenomena.

These elements of the invention are described in greater detail below.

1. An excimer laser, the wavelength of which is in the ultraviolet (UV, 248 and 308 nm) range, is used as energy source. Accordingly, all available dyes can be pumped with a high pulse energy.

2. The wavelength of the laser system becomes tuneable as a result of the connection of a dye laser downstream. Such tuneability is necessary for the purposes of the method according to the invention
   (a) on physical grounds, since the dimensions of the focussed light are dependent upon the wavelength;
   (b) on biological grounds, since undesirable secondary effects in the processing of biological material (eg. damage to genetic material) are highly dependent on the wavelength. Since the dye laser is pumped by an excimer laser of high power, continuous tuneability is assured over a wavelength range from 100 to 1500 nm. The high pumping energies permit not only direct excitation of dyes but also frequency doubling, Raman shifting and frequency mixing of the dye laser pulses.

3. The laser radiation emitted by the dye laser exhibits a very low beam divergence, and can therefore be focussed to the limit of what is physically possible. In the method according to the invention, the focussing is achieved in that the light is fed through the incident light illumination channel into a microscope and is focussed by the microscope objective onto the object slide of the microscope. Because of the very short focal length of the objective, the focal spot produced in this manner has a very small depth (dimension in the direction of the radiation). Thus, by the use of a movable object stage and by variation of the focal plane the focal spot may be moved in three dimensions relative to the object. This can for example be utilized to carry out microsurgical operations on biological cells, including those situated in relatively deep cell layers.

4. As a result of diffraction phenomena at the diaphragm apertures, the focal spot does not appear in the focal plane simply as a circular disk, but is surrounded by a system of diffraction rings, the relative spacing of which corresponds precisely to the wavelength of the light employed and which contain several per cent of the total energy of the focussed light. In the case of the pulses generated by the combination of items 1 to 3, the diffraction rings are so intense that from about 5 to 10 of these rings can be used to cut biological material (eg. chromosomes). Since the spacing of the diffraction rings is determined by the wavelength of the light, accurate cuts can be applied to elongate biological objects. As a result of the tuneability of the laser system, the spacing of the cuts may be freely selected within the available wavelength range. Because of the possibility of operating also in UV with intense pulses, very small spacings between cuts may in particular be chosen. Since threshold effects play a part in cutting by means of diffraction rings, the cuts are very fine, the thickness of the cuts being substantially smaller than the wavelength of the light employed.

With the invention, it became possible for the first time to apply to elongate biological material fine equidistant cuts (see the figure), the spacing of which can be predetermined by the choice of the pulse energy. Since several cuts can be made simultaneously, and since new objects can be introduced into the beam quickly by the application of a touch-sensitive screen in conjunction with a computer-controlled scanning stage, the processing of a large number of biological objects is moreover possible.

USE EXAMPLES

1. The cutting of chromosomes, which are visible in an optical microscope, for microcloning experiments. As a result of this technique, the position of specific genes on specific chromosome sections may be determined in a simpler manner than with the customary methods of molecular biology.

2. The cutting of chromosomes from healthy cells at typical breaking points, which occur in the case of cancer diseases, eg. Burkitt lymphoma (in this case, only a single diffraction ring is used). Such experiments can provide information on whether chromosome ruptures are a cause or a consequence of diseases.

3. Production of roughly monodisperse oligonucleosomes. Nucleosomes, roughly disk-shaped protein-DNA complexes having a molecular weight of 204,000, are the frequently repeating components of chromatin, the gene material of higher organisms, which becomes folded over into the chromosome during cell division. Chromatin fragments (=oligonucleosomes) of clearly defined length are ideally required for the study of such folding processes, which are also of importance if it is to be possible to read individual genes. In methods of production which are based on molecular biology or biochemistry and which are in current use, fragments containing $40 \pm 10$ nucleosomes are for example considered as "homogeneous". When the method according to the invention is employed, a considerably improved homogeneity ($40 \pm 1$) may be achieved at a mean nucleosome spacing of 14 nm at a wavelength of 560 nm.

4. Intermediate filaments, microtubulies or filamentous bacteriophages may be cut in a similar manner, with the object of using the resulting short fragments of these roughly cylindrical structures in the production of crystals for X-ray diffraction experiments. Formerly, only X-ray diffraction experiments on fibers were possible in the case of such elongate objects; however, the latter experiments provided substantially less information. Since in the case of the applications described under items 3 and 4 the objects to be processed are not visible, they must be aligned in a current or in an electric field and cut "blind."

5. The figure shows chromosomes derived from human lymphocytes. Some chromosomes (small arrows) are processed by the entire radiation, so that the entire diffraction pattern becomes visible in the lesions. In the case of the chromosome marked by the large arrow, the small central diffraction disk was located outside the chromosome, so that only a roughly parallel pattern of cuts can be seen. The wavelength of the light employed was 570 nm.

We claim:

1. A method for the performance of microsurgery in the form of the application of cuts, perforations, and/or microlesions, to biological material, such as, for example, cell agglomerates, individual cells or chromosomes, said method comprising the steps of providing a high-magnification microscope having an objective of short focal length with diaphragm apertures, providing a tunable laser system including a high-energy pumping laser and a high-energy dye laser pumped by said pumping laser, feeding laser pulses output by the laser system into said microscope and focusing said pulses on said material through said objective so that diffraction rings are generated by said diaphragm apertures, the relative spacing of said rings corresponding to the wavelength of the laser light employed, and using the nth order diffraction maxima (n=1,2,3, ... ) of the laser pulses for performing said microsurgery with spatial resolutions at the theoretically possible limit.

2. A method as claimed in claim 1, wherein the laser pulses have a duration of from $10^{-12}$ to $10^{-3}$ sec and a pulse energy of up to $15 \cdot 10^{-3}$ joule per pulse, and are tunable in wavelength in the range from 100 to 1500 nm.

* * * * *

UNITED STATES PATENT AND TRADEMARK OFFICE
CERTIFICATE OF CORRECTION

PATENT NO. : 4,748,980
DATED : June 7, 1988
INVENTOR(S) : Christoph Cremer et al.

It is certified that error appears in the above-identified patent and that said Letters Patent is hereby corrected as shown below:

Column 4, line 50, "15·10---3" should read -- $15 \cdot 10^{-3}$

Signed and Sealed this

Twenty-second Day of November, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,748,980

DATED : Jun. 7, 1988

INVENTOR(S) : Cremer et al.

It is certified that error appears in the above-identified patent and that said Letters Patent is hereby corrected as shown below:

On the title page Insert
-- [73] Assignee: BASF Aktiengesellschaft Ludwigshafen, Fed. Rep. of Germany --

Signed and Sealed this

Twenty-eighth Day of March, 1989

Attest:

DONALD J. QUIGG

Attesting Officer     Commissioner of Patents and Trademarks